United States Patent [19]
Coe

[11] Patent Number: 6,065,474
[45] Date of Patent: May 23, 2000

[54] COMPLIANCE RING

[75] Inventor: Matthew Coe, Asbury, N.J.

[73] Assignee: Pharma Design, Inc., Warren, N.J.

[21] Appl. No.: 09/037,730

[22] Filed: Mar. 9, 1998

[51] Int. Cl.[7] .............................. A62B 7/00; G01D 11/00
[52] U.S. Cl. .............................. 128/205.23; 128/200.23; 116/280
[58] Field of Search .................. 128/200.23, 205.23, 128/200.14, 200.22, 200.24, 203.12, 203.22, 204.11, 204.12, 909; 116/280, 307, 308, 311–315, 319; 222/420, 23, 321.6; 206/459.1, 534

[56] References Cited

FOREIGN PATENT DOCUMENTS 27011 of 1909 United Kingdom .................. 116/308

*Primary Examiner*—Aaron J. Lewis
*Assistant Examiner*—Teena Mitchell
*Attorney, Agent, or Firm*—Notaro & Michalos P.C.

[57] ABSTRACT

A compliance ring for indicating into which nostril medication has last been sprayed, comprises fixed and movable rings engaged to each other and held between the actuator and the reservoir bottle of the dispenser of the medication. The fixed ring has a cylindrical skirt which is interrupted by a rectangular recess and a movable ring has an outwardly projecting indicator which, with rotation of the movable ring in the fixed ring, moves from one position to the other. In one position, the indicator registers with the letter "R" on the upper surface of the fixed ring, and in the opposition position, the indicator registers with the letter "L". The letters "L" and "R" indicate left and right nostrils which have received medication or are meant to receive medication next.

6 Claims, 2 Drawing Sheets

COMPLIANCE RING

FIELD AND BACKGROUND OF THE INVENTION

The present invention relates, in general, to dispensers for dispensing medication to a subject or patient and, in particular, to a device for use on dispensers for dispensing medication to one nostril of a patient, or the other, so that the patient knows which nostril to use in a subsequent medication step.

Dispensers are known for dispensing a medicated spray to the nostrils of a patient. It is conventional for the medication to be alternated from one nostril to the other to avoid irritation. In some circumstances, one nostril might be preferred over the other for receiving the medication.

Other forms of medication may also be used in one or both eyes or at other locations on the body. It would be useful to have a simple mechanism which is attached to the dispenser, for indicating to the subject or patient using the dispenser, which location of the body was treated last, or should be treated next with the medication.

SUMMARY OF THE INVENTION

An object of the present invention is to provide a compliance ring for medication to be applied by a dispenser to at least two different locations of a subject, comprising: a fixed ring adapted to be fixed to the dispenser and having a first indicator; and a movable ring movably mounted with respect to the fixed ring and movable between at least two positions with respect to the fixed ring, corresponding to at least two different locations of the subject to which the medication is to be applied, the movable ring having a second indicator alignable with the first indicator for indicating a different one of the at least two different locations, in each of the at least two positions of the movable ring.

A further object of the present invention is to fix the fixed ring between an applicator portion and a reservoir portion of the dispenser, and to rotatably mount the movable ring to the fixed ring. Advantageously, the first indicator is in the form of the letters "L" and "R" which are spaced around the circumference of the fixed ring. The second indicator is a projection extending outwardly from the movable ring and movable either to be aligned with the "L" or the "R" in the fixed ring to indicate whether the left or right location of the subject has been last medicated, for example, the left or right nostril of the subject's nose when the dispenser is a nasal spray dispenser.

The invention is equally applicable to other locations of the body, such as the eyes in the case of an eyedrop dispenser, or to other types of dispensers for applying medication to various other parts of the body.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 3:
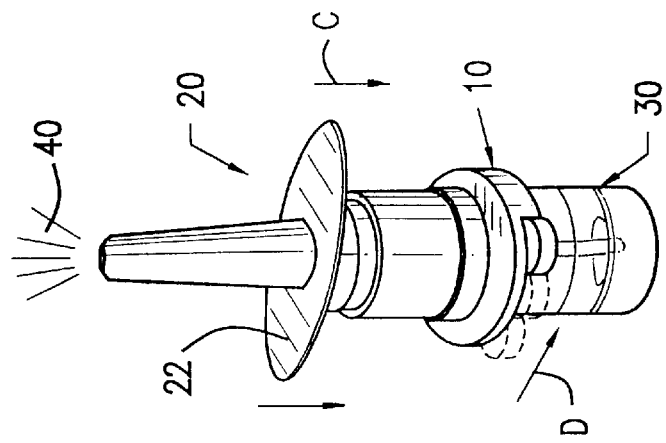
FIG. 3 is a perspective view of the assembled compliance ring and dispenser, in accordance with the present invention.
Figure 2:
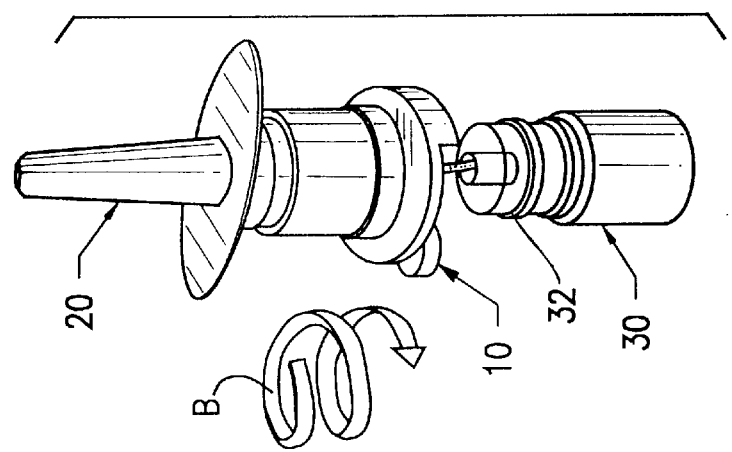
FIG. 2 is an exploded view showing the applicator attached to the compliance ring and about to be connected to a reservoir portion of the dispenser.
Figure 1:
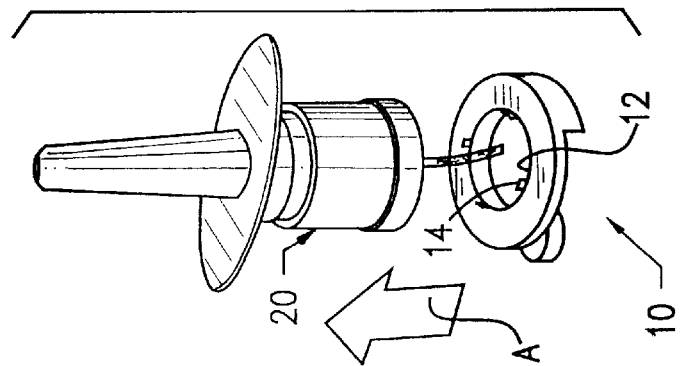
FIG. 1 is a perspective exploded view of the applicator portion of a dispenser and a compliance ring, in accordance with the present invention.

Referring to the drawings in particular, the invention embodied in FIGS. 1, 2 and 3 comprises a compliance ring generally designated 10 for engagement against the undersurface of an actuator 20 for spraying medication into a nostril of a subject or patient. Compliance ring 10 has a central opening 12 for receiving the neck of a reservoir or bottle of the dispenser, and a plurality of upstanding teeth 14 around the perimeter of opening 12. Compliance ring 10 is moved in the direction of arrow A, into engagement with the lower perimeter of the actuator 20 and is centered by teeth 14.

As shown in FIG. 2, the now assembled compliance ring 10 with actuator 20, is screwed in the direction of arrow B down onto the upper threaded neck 32 of the reservoir 30 of the dispenser. The dispenser is normally comprised of reservoir 30 and actuator 20, but according to the present invention, the compliance ring 10 is interposed between these two parts.

FIG. 3 illustrates the assembled dispenser 20, 30 with compliance ring 10. In use, ears 22 of actuator 20 are pressed downwardly in the direction of arrow C to pump an aerosol spray 40 of medication into one nostril of the patient. In accordance with the invention, an indicator tab on a rotatable ring in the compliance ring 10, is rotated in the direction of arrow D, to indicate that the previous spray had been made to the left nostril of the subject and that the next spray application is for the right nostril.

Figure 4:
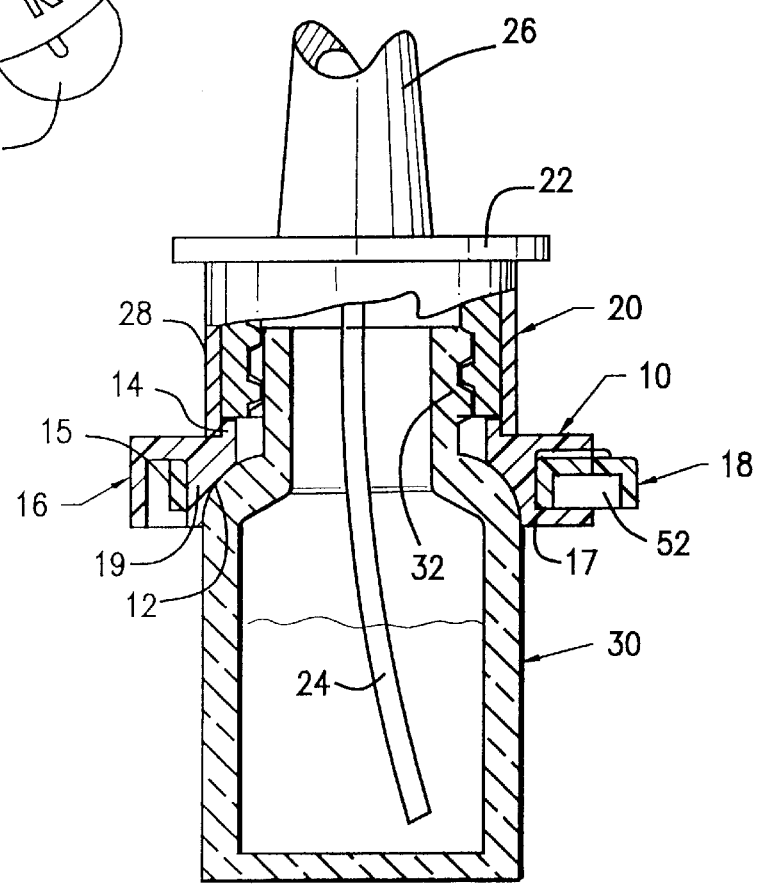
FIG. 4 is a partial sectional view of the dispenser with compliance ring attached thereto.

FIG. 4 illustrates the threaded engagement between actuator 20 and the neck 32 of reservoir 30, and the captured compliance ring 10 therebetween. Actuator 20 includes a tube 24 which extends down into the liquid medication in reservoir 30 so that when ears 22 are pressed downwardly, they pump an aerosol of liquid into the nostril through a conical openended nozzle 26.

Figure 6:
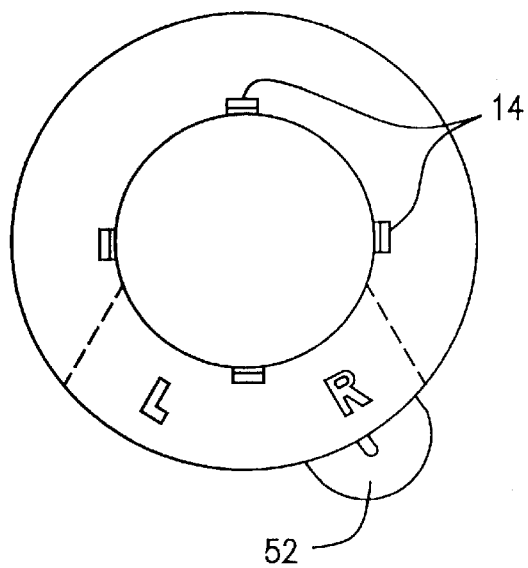
FIG. 6 is a top plan view of the compliance ring of the present invention.
Figure 5:
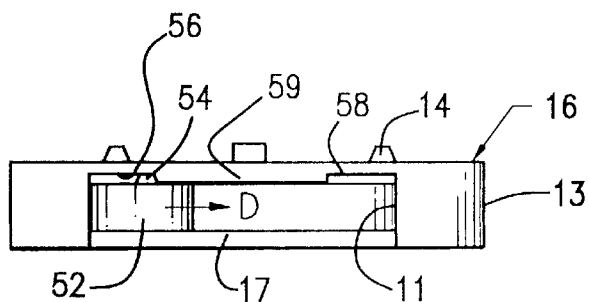
FIG. 5 is a front elevational view of the compliance ring showing the engagement of the movable ring in a selected position with respect to the fixed ring.

As shown in FIGS. 4 and 6, four teeth 14, spaced around the opening 12 of compliance ring 10, center the compliance ring on the outer cylinder 28 of actuator 20. The inner contour of opening 12 is shaped to engage onto the circular and rounded shoulder of the cylindrical reservoir 30 and, through the screw thread connection between actuator 20 and reservoir 30, a fixed ring 16 of compliance ring 10 is fixed in position. A movable ring 18 is rotatably mounted within fixed ring 16 and is held for rotation on an annular hub 19 of fixed ring 16, by a circular outwardly projecting bead 17. Movable ring 18 comprises an inner ring 15 which slidably engages around the outer surface of hub 19 and is held in rotatable engagement with fixed ring 16 by the bead 17. As best shown in FIG. 5, an outer cylindrical skirt 13 of movable ring 18 has a continuous cylindrical shape except for a rectangular cutout area 11. Cutout area 11 receives an indicator projection 52 extending outwardly from the perimeter of ring 15. Indicator 52 can move in the direction of arrow D in FIGS. 3 and 5, between opposite ends of recess 11 to align with a first indicator as shown in FIG. 6 in the form of the letters "L" or "R" indicating left or right nostrils. An elongated detent 54 extends upwardly from the upper surface of indicator 52 and engages in a slot-shaped enlargement or interruption 56 in the upper area of recess 11. Enlargement or interruption 56 is mirrored by a second enlargement or interruption 58 on the opposite side of a platform 59 under which detent 54 is forced to move when ring 18 is rotated from one position, shown in FIG. 5, to the opposite position, shown in FIG. 6, in the direction of arrow D. This movement and rotation is confined by bead 17 which does not permit the movable ring 18 from being disengaged from the fixed ring 16.

The compliance ring 10, including its fixed and movable rings 16, 18, are advantageously made of injection-molded plastics, such as polypropylene or other appropriate plastic material. Dispenser 20, 30 is available on the market, for example, in the form of a Miacalcin bottle.

Other embodiments envisioned include the adaptation of the compliance ring 10 to squeeze bottles and eye or nose droppers, where it would be advantageous to have the indicator show which side body part was last treated. Accordingly, while a particular bottle type is disclosed for use with the invention, other bottles having different dispensers or actuating mechanisms may be used with the compliance ring 10.

Further, the four teeth 14 may be replaced by another centering mechanism, such as foam tape, a single post, or a spaced pair of arcuate ridges positioned around the opening.

While a specific embodiment of the invention has been shown and described in detail to illustrate the application of the principles of the invention, it will be understood that the invention may be embodied otherwise without departing from such principles.

What is claimed is:

1. A compliance ring for a dispenser containing a medication to be applied to at least two different locations of a subject, the compliance ring comprising a fixed ring adapted to be fixed to such a dispenser and having a first indicator; and a movable ring movably mounted with respect to the fixed ring and movable between at least two positions with respect to the fixed ring, corresponding to at least two different locations of such a subject to which the medication is to be applied, the movable ring having a second indicator alignable with the first indicator for indicating a different one of the at least two different locations, in each of the at least two positions of the movable ring.

2. A compliance ring according to claim 1, wherein said fixed ring comprises an inner hub and an outer skirt, said movable ring being rotatably mounted on said hub, said skirt contained an interruption, said first indicator comprising markings on an upper surface of said fixed ring and said second indicator comprising a radial projection extending outwardly of the interruption and movable between one end of the interruption and an opposite end of the interruption.

3. A compliance ring according to claim 2, including a bead around a lower periphery of the hub for retaining the movable ring to the hub.

4. A compliance ring according to claim 3, wherein the fixed ring includes an opening for receiving a neck of a bottle of a dispenser, the fixed ring including means for centering the compliance ring on an actuator of such a dispenser.

5. A compliance ring according to claim 4, including a detent on the second indicator for holding the movable ring in one of the plurality of positions with respect to the fixed ring.

6. A compliance ring according to claim 4, wherein the means for centering comprises a plurality of upwardly extending teeth.

* * * * *